(12) United States Patent
Jagerovic et al.

(10) Patent No.: US 8,193,223 B2
(45) Date of Patent: Jun. 5, 2012

(54) 1,2,3-TRIAZOLE DERIVATIVES AS SIGMA RECEPTOR INHIBITORS

(75) Inventors: Nadine Jagerovic, Madrid (ES); Cristina Ana Gomez-De La Oliva, Madrid (ES); Maria Pilar Goya-Laza, Madrid (ES); Alberto Dordal Zueras, Barcelona (ES); Maria Rosa Cuberes-Altisent, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 371 days.

(21) Appl. No.: 12/514,213

(22) PCT Filed: Nov. 7, 2007

(86) PCT No.: PCT/EP2007/062010
§ 371 (c)(1),
(2), (4) Date: Aug. 25, 2009

(87) PCT Pub. No.: WO2008/055933
PCT Pub. Date: May 15, 2008

(65) Prior Publication Data
US 2010/0004265 A1  Jan. 7, 2010

(30) Foreign Application Priority Data
Nov. 10, 2006 (EP) .................................. 06380289

(51) Int. Cl.
*A61K 31/4192* (2006.01)
*C07D 403/06* (2006.01)

(52) U.S. Cl. ........................ 514/359; 548/255

(58) Field of Classification Search ............. 514/217.09; 548/255
See application file for complete search history.

(56) References Cited

U.S. PATENT DOCUMENTS 6,638,954 B2   10/2003   Kadaba

FOREIGN PATENT DOCUMENTS

| WO | 9109594 A1 | 7/1991 |
| WO | 0236119 A1 | 5/2002 |
| WO | WO2007056210 | * 5/2007 |

OTHER PUBLICATIONS

Bryn, Solid State Chemistry of Drugs, 2nd edition, 1999, SSCI, Inc, Chapter 10, Polymorphs, p. 232-247.*
Bundgaard, Design of Prodrugs, 1985, Elsevier, Chapter 1, p. 1-4.*
Maurice, Pharmacology of Sigma-1 Receptors, 2009, Pharmacol Ther., 124(2), p. 195-206.*
Mei, σ1 Receptor Modulation of Opioid Analgesia in the Mouse, 2002, Journal of Pharmacology and Experimental Therapeutics, vol. 300, No. 4, p. 1070-1074.*
Walker, J.M., et al., "Sigma Receptors: Biology and Function", Pharmacological Reviews, 1990, 42, 355.
Snyder, S.H., et al., "Receptor Mechanisms in Antipsychotic Drug Action: Focus on Sigma Receptors", J. Neuropsychiatry, 1989, 1, 7.
Quirion, R., et al., "A proposal for the classification of sigma binding sites", Trends Pharmacol. Sci., 1992, 13:85-86.
Hanner, M., et al., "Purification, molecular cloning, and expression of the mammalian sigma1-binding site", Proc. Natl. Acad. Sci., 1996, 93:8072-8077.
Calderone, V., et al., "Benzoyl and/or benzyl substituted 1,2,3-triazoles as potassium channel activators. VIII", Eur. J. Med. Chem., 2005, 40, 521-528.
Rossi, L., et al., "Glycosidase inhibition by 1-glycosyl-4-phenyl triazoles", Bioorg. Med. Chem. Lett., 2005, 15, 3596-3599.
Salameh, B.A., et al., "3-(1,2,3-Triazol-1-yl)-1-thio-galactosides as small, efficient, and hydrolytically stable inhibitors of galectin-3", Bioorg. Med. Chem. Lett., 2005, 15, 3344-3346.
Kim, D., et al., "Synthesis and biological evaluation of novel 2-pyridinyl-[1,2,3]triazoles as inhibitors of transforming growth factor β1 type 1 receptor", Bioorg. Med. Chem. Lett., 2004, 14, 2401-2405.
Brik, A., et al., "1,2,3-Triazole as a Peptide Surrogate in the Rapid Synthesis of HIV-1 Protease Inhibitors", Chembiochem, 2005, 6, 1167-1169.
Kolb, C., et al., "Olefins, spring-loaded electrophiles, and heteroatom connections are key elements in a fast, modular, process-driven approach to molecular discovery", Angew. Chem. Int. Edit., 2001, 40, 2004-2021. Prashad, M., et al., "1,2,3-Triazole as a safer and practical substitute for cyanide in the Bruylants reaction for the synthesis of tertiary amines containing tertiary alkyl or aryl groups", Tetrahedron Lett., 2005, 46, 5455-5458.
Kozima, S., "Formation of Organotin-Nitrogen Bonds", J. Organomet. Chem., 1972, 44, 117-126.
Hitomi, T., "Formaton of Organotin-Nitrogen Bonds", J. Organomet. Chem., 1977, 127, 273-280.
Nguefack, J.F., et al., "An Efficient Palladium-Catalysed Coupling of Terminal Alkynes with Aryl Halides under Jeffery's Conditions", Tetrahedron Lett., 1996, 37, 5527-5530.
DeHaven-Hudkins, D.L., et al., "Characterization of the binding of [3H](+)-pentazocine to σ recognition sites in guinea pig brain", Eur. J. Pharmacol., 1992, 227, 371-378.
Lowry, O.H., et al., "Protein Measurement With the Folin Phenol Reagent", J. Biol. Chem., 1951, 193, 265.
Perabo, F.G., et al., "Carboxyamido-triazle (CAI) Reverses the Balance between Proliferation and Apoptosis in a Rat Bladder Cancer Model", Anticancer Res., 2005, 25, 725-729.
International Search Report for PC/EP2007/062010, dated Mar. 17, 2008.

* cited by examiner

*Primary Examiner* — Andrew D Kosar
*Assistant Examiner* — Karen Cheng
(74) *Attorney, Agent, or Firm* — Hoffmann & Baron, LLP

(57) ABSTRACT

The invention relates to compounds having pharmacological activity towards the sigma receptor, and more particularly to 1,2,3-triazole derivatives of formula (I) and to processes of preparation of such compounds, to pharmaceutical compositions comprising them, and to their use in therapy and prophylaxis, in particular for the treatment of psychosis or pain.

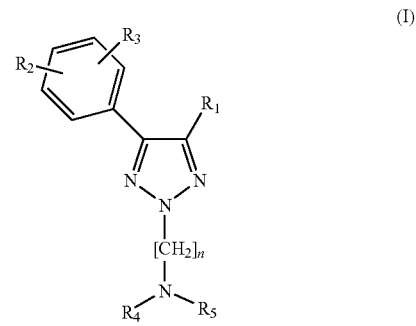

17 Claims, No Drawings

1,2,3-TRIAZOLE DERIVATIVES AS SIGMA RECEPTOR INHIBITORS

CROSS-REFERENCE TO RELATED APPLICATIONS

This application is the National Stage of International Application No. PCT/EP2007/062010, filed Nov. 7, 2007, which claims the benefit of European Application No. 06380289.6, filed Nov. 10, 2006, the contents of which are incorporated by reference herein.

FIELD OF THE INVENTION

The present invention relates to compounds having pharmacological activity towards the sigma receptor, and more particularly to some 1,2,3-triazole derivatives, to processes of preparation of such compounds, to pharmaceutical compositions comprising them, and to their use in therapy and prophylaxis of a disease mediated by sigma receptor.

BACKGROUND OF THE INVENTION

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psycosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application No WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

With regard to the chemical structure of the compounds described in the present patent application, it is to be highlighted that the 1,2,3-triazole ring system has been the subject of considerable research mainly due to the pharmacological properties shown by some of its derivatives and also because of its usefulness in synthetic organic chemistry. Among the first, recent reports have dealt with 1,2,3-triazoles as antimicrobial agents, as potassium channel activators (Calderone, V. et al. *Eur. J. Med. Chem.*, 2005, 40, 521-528). 1,2,3-Triazole derivatives of glycosyl and galactoside have been respectively described as glycosidase (Rossi, L. L. et al., *Bioorg. Med. Chem. Lett.*, 2005, 15, 3596-3599) and galactin-3 (Salameh, A. et al., *Bioorg. Med. Chem. Lett.*, 2005, 15, 3344-3346) inhibitors. 2-Pyridinyl-1,2,3-triazoles have been described as transforming growth factor beta 1 type 1 receptor (Kim, J. et al, *Bioorg. Med. Chem. Lett*, 2004, 14, 2401-2405). In addition, a 1,2,3-triazole-4-carboxamide derivative (CAI) has been identified as an orally bioavailable calcium influx and signal transduction inhibitor with anti-angiogenic and anti-metastatic properties in different human tumours (Perabo, F. G., et al., *Anticancer Res.*, 2005, 25, 725-729). The 1,2,3-triazole moiety has been identified as an effective replacement for a peptide group in HIV-1 protease inhibitors (Brik, J. et al., *Chembiochem*, 2005, 6, 1167-1169). Concerning synthetic issues, 1,2,3-triazoles can be considered the ideal representatives of "click chemistry" (Kolb, C. et al., *Angew. Chem. Int. Edit.*, 2001, 40, 2004-2021), and recently, 1,2,3-triazole has been used as a safer and practical alternative to cyanide in Bruylants reaction (Prashad M. et al., *Tetrahedron Lett.*, 2005, 46, 5455-5458).

However, none of these documents suggests the effect of these compounds on the sigma receptor.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of structurally distinct triazole derivatives which are particularly selective inhibitors of the sigma-1 receptor. The compounds present a 1,2,3-triazole group which are characterized by the substitution in the 2 position by an alkyl chain which ends in an amine type substituent.

In one aspect the invention is directed to a compound of the formula I:

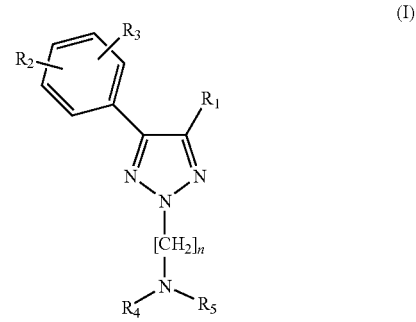

wherein
- $R_1$ is selected from hydrogen, $C_1$-$C_6$ alkyl and substituted or unsubstituted aryl;
- $R_2$ and $R_3$ are independently selected from hydrogen and halogen;
- $R_4$ and $R_5$ are independently selected from hydrogen, $C_1$-$C_6$ alkyl and cycloalkyl, or form, together with the nitrogen to which they are attached, a substituted or unsubstituted heterocyclyl group; with the proviso that $R_4$ and $R_5$ are not both hydrogen,
- n in an integer selected from 1, 2, 3, 4, 5, 6, 7 and 8, or a pharmaceutically acceptable salt, stereoisomer, prodrug or solvate thereof.

In one embodiment, it is preferred that $R_1$ is hydrogen, $C_1$-$C_3$ alkyl, unsubstituted phenyl or a phenyl substituted by a $C_1$-$C_3$ alkyl, more preferably hydrogen, methyl, phenyl or 4-methyl-phenyl.

In another preferred embodiment, $R_2$ and $R_3$ are independently selected from hydrogen and halogen, more preferably hydrogen and chloride. In another preferred embodiment one of $R_2$ and $R_3$ is in the para position of the phenyl group.

Further in another preferred embodiment $R_4$ and $R_5$ form, together with the nitrogen to which they are attached, a substituted or unsubstituted heterocyclyl group, preferably selected from piperidine, piperazine, imidazole, pyrrolidine, morpholine and azepane.

Further, in a preferred embodiment n is preferably 2, 3, 4, 5 or 6.

In a second aspect the invention is directed to a process for the preparation of a compound of formula I or a salt, isomer, prodrug or solvate thereof.

In another aspect the invention is directed to a pharmaceutical composition which comprises a compound as defined above or a pharmaceutically acceptable salt, isomer, prodrug or solvate thereof, and a pharmaceutically acceptable carrier, adjuvant or vehicle.

In a further aspect the invention is directed to the compound of formula I as defined above for its use as a medicament.

Another aspect of the invention is the use of a compound of formula I as defined above in the manufacture of a medicament for the treatment or prophylaxis of a sigma-1 receptor mediated disease or condition.

In a preferred embodiment the compound of formula I is used in the manufacture of a medicament for the treatment of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

In a more preferred embodiment the medicament is for the treatment of pain, especially neuropathic pain, inflammatory pain or other pain conditions involving allodynia and/or hyperalgesia.

In another aspect, the present invention refers to a compound of formula (I) as defined above for its use in the treatment of the diseases mentioned above.

Finally, in another aspect, the invention relates to the use of a compound of formula (I) as defined above as pharmacological tool, as anxiolytic or as immunosuppressant.

The above mentioned preferences and embodiments can be combined to give further preferred compounds or uses.

DETAILED DESCRIPTION OF THE INVENTION

The typical compounds of this invention effectively and selectively inhibit the sigma-1 receptor.

In the present description the following terms have the meaning indicated:

"$C_1$-$C_6$ alkyl" refers to a straight or branched hydrocarbon chain radical consisting of carbon and hydrogen atoms, containing no unsaturation, having one to six carbon atoms, and which is attached to the rest of the molecule by a single bond, e.g., methyl, ethyl, propyl, isopropyl, n-butyl, sec-butyl, tert-butyl, pentyl, hexyl, etc.

"Heterocyclyl" refers to a substituted or unsubstituted stable 3- to 8-membered ring radical which consists of carbon atoms and from one to three heteroatoms selected from the group consisting of nitrogen, oxygen and sulfur, preferably a 4- to 7-membered ring with one or more heteroatoms, more preferably a 5, 6 or 7-membered ring with one or more heteroatoms. It may be partially of fully saturated or aromatic. Additionally, the heterocycle may be also monocyclic, bicyclic or tricyclic ring system, which may include fused ring systems; and the nitrogen, carbon or sulfur atoms in the heterocyclyl radical may be optionally oxidised; the nitrogen atom may be optionally quaternized. Examples of such heterocycles include, but are not limited to, azepines, benzimidazole, benzothiazole, isothiazole, imidazole, indole, piperidine, piperazine, purine, quinoline, thiadiazole, morpholine, pyrrole, pyrazole, oxazole, isoxazole, triazole, imidazole, etc.

The heterocyclyl group may be substituted at one or more available positions by one or more suitable groups, e.g., halogen such as fluoro, chloro, bromo and iodo; cyano; hydroxyl; nitro; alkyl groups including those groups having 1 to about 12 carbon atoms or from 1 to about 6 carbon atoms and more preferably 1-3 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

"Cycloalkyl" refers to a stable 3- to 10-membered monocyclic or bicyclic radical which is saturated or partially saturated, and which consists solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Halo" refers to bromo, chloro, iodo or fluoro.

In one embodiment, it is preferred that $R_1$ is hydrogen, $C_1$-$C_3$ alkyl, unsubstituted phenyl or a phenyl substituted in para position by a $C_1$-$C_3$ alkyl, more preferably hydrogen, methyl, phenyl or 4-methyl-phenyl.

In another preferred embodiment, $R_2$ and $R_3$ are independently selected from hydrogen and halogen, more preferably hydrogen and chloride. In another preferred embodiment one of $R_2$ and $R_3$ is in the para position of the phenyl group.

Further in another preferred embodiment $R_4$ and $R_5$ form, together with the nitrogen to which they are attached, a substituted or unsubstituted heterocyclyl group, preferably selected from piperidine, piperazine, imidazole, pirrolidine, morpholine and azepane.

Further, in another preferred embodiment n is 2, 3, 4, 5 or 6.

Preferred compounds of formula I are the following:
1-{3-[4-(4-chloro-phenyl)-5-phenyl-[1,2,3]triazol-2-yl]-propyl}-piperidine;
1-[3-[4-(p-chlorophenyl)-5-phenyl-([1,2,3]triazol-2-yl)propyl]-imidazole;
1-[3-[4-(3,4-dichlorophenyl)-5-phenyl-([1,2,3]triazol-2-yl)propyl]-pyrrolidine;
1-{3-[4-(2,4-dichloro-phenyl)-5-p-tolyl-[1,2,3]triazol-2-yl]-propyl}-piperidine;
4-{3-[4-(2,4-dichloro-phenyl)-5-p-tolyl-[1,2,3]triazol-2-yl]-propyl}-morpholine;
1-[3-[4-(p-chlorophenyl)-5-phenyl-([1,2,3]triazol-2-yl)propyl]-homopiperidine;
1-[3-[4-(3,4-dichlorophenyl)-5-phenyl-([1,2,3]triazol-2-yl)propyl]-imidazole;
1-[3-[4-(3,4-dichlorophenyl)-5-phenyl-([1,2,3]triazol-2-yl)propyl]-homopiperidine;
cyclohexyl-[3-[4-(3,4-dichlorophenyl)-5-phenyl-([1,2,3]triazol-2-yl)propyl]-amine
1-{4-[4-(4-chloro-phenyl)-5-phenyl-[1,2,3]triazol-2-yl]-butyl}-piperidine;
1-{2-[4-(4-chloro-phenyl)-5-phenyl-[1,2,3]triazol-2-yl]-ethyl}-piperidine;
4-{2-[4-(4-chloro-phenyl)-5-phenyl-[1,2,3]triazol-2-yl]-ethyl}-morpholine;
1-[2-[4-(p-chloro-phenyl)-5-phenyl-([1,2,3]triazol-2-yl)ethyl]-pyrrolidine;
1-{5-[4-(4-chloro-phenyl)-5-phenyl-[1,2,3]triazol-2-yl]-pentyl}-piperidine;
1-[3-[4-(p-chloro-phenyl)-5-phenyl-([1,2,3]triazol-2-yl)propyl]-pyrrolidine;
1-{3-[4-(4-chloro-phenyl)-5-phenyl-[1,2,3]triazol-2-yl]-propyl}-4-phenyl-piperidine;
4-{3-[4-(4-chloro-phenyl)-5-phenyl-[1,2,3]triazol-2-yl]-propyl}-morpholine;
1-{3-[4-(4-chloro-phenyl)-5-phenyl-[1,2,3]triazol-2-yl]-propyl}-4-phenyl-piperazine;
1-[3-(4-methyl-5-phenyl-[1,2,3]triazol-2-yl)-propyl]-piperidine;
1-[3-(4-phenyl-[1,2,3]triazol-2-yl)-propyl]-piperidine;
1-{3-[4-(4-bromo-2-fluoro-phenyl)-[1,2,3]triazol-2-yl]-propyl}-piperidine;
1-[2-(4-phenyl-2H-[1,2,3]triazol-2-yl)-ethyl]-azepane;
cyclohexyl-[3-(4-phenyl-2H-[1,2,3]triazol-2-yl)propyl]-amine;
1-[4-(4-phenyl-2H-[1,2,3]triazol-2-yl)-buty]-azepane;
1-[3-(4-phenyl-2H-[1,2,3]triazol-2-yl)-propyl]-azepane;
4-[3-(4-phenyl-2H-[1,2,3]triazol-2-yl)-propyl]-morpholine;
1-[2-(4-phenyl-2H-[1,2,3]triazol-2-yl)-ethyl]-piperidine;
or a pharmaceutically acceptable salt, isomer, prodrug or solvate thereof.

Additionally, in another preferred embodiment of the invention the compound of formula I is an oxalic salt thereof.

Preferred salts of the compounds of formula I are the following:
1-[2-(4-phenyl-2H-[1,2,3]-triazol-2-yl)-ethyl]-azepanium oxalate;
cyclohexyl-[3-(4-phenyl-2H-[1,2,3]-triazol-2-yl)propyl]-ammonium oxalate;
1-[4-(4-phenyl-2H-[1,2,3]-triazol-2-yl)-butyl]-azepanium oxalate;
1-[3-(4-phenyl-2H-[1,2,3]-triazol-2-yl)-propyl]-azepanium oxalate;
4-[3-(4-phenyl-2H-[1,2,3]-triazol-2-yl)-propyl]-morpholin-4-ium oxalate;
1-[2-(4-phenyl-2H-[1,2,3]-triazol-2-yl)-ethyl]-piperidinium oxalate;

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon or $^{15}N$-enriched nitrogen are within the scope of this invention.

The term "pharmaceutically acceptable salts, solvates, prodrugs" refers to any pharmaceutically acceptable salt, isomer, solvate, prodrug or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, isomers, solvates, prodrugs and derivatives can be carried out by methods known in the art.

For instance, pharmaceutically acceptable salts of compounds provided herein are synthesized from the parent compound which contains a basic moiety by conventional chemical methods. Generally, such salts are, for example, prepared by reacting the free base forms of these compounds with a stoichiometric amount of the appropriate acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate.

Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula I is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula I, their salts, isomers, prodrugs or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula I, or of its salts, isomers, solvates or prodrugs.

The compounds of the present invention represented by the above described formula (I) may include enantiomers depending on the presence of quiral centres. The single isomers, enantiomers or diastereoisomers and mixtures thereof fall within the scope of the present invention.

The compounds of formula I defined above can be obtained by available synthetic procedures. In a particular embodiment of the invention, a process to prepare the compounds of formula (I) or a salt, isomer, prodrug or solvate thereof, comprises the alkylation reaction of a compound $NHR_4R_5$ with a compound of formula (IV):

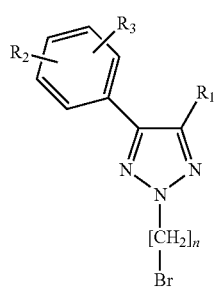

(IV)

wherein:

$R_1$ is selected from hydrogen, $C_1$-$C_6$ alkyl and substituted or unsubstituted aryl;

$R_2$ and $R_3$ are independently selected from hydrogen and halogen;

$R_4$ and $R_5$ are independently selected from hydrogen, lower alkyl and cycloalkyl, or form, together with the nitrogen to which they are attached, a substituted or unsubstituted heterocyclyl group; and n is an integer selected from 1, 2, 3, 4, 5, 6, 7 and 8, with the proviso that $R_4$ and $R_5$ are not both hydrogen.

Compounds of formula (IV) can be prepared by alkylation of a compound of formula (III):

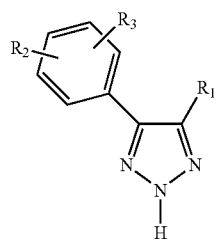

(III)

with n-alkyl di-bromide of formula $[Br—(—CH_2—)_n—Br]$, wherein $R_1$, $R_2$, $R_3$ and n are as defined above.

This reaction takes place under basic conditions, for example in the presence of hydroxides such as potassium hydroxide, using a phase transfer catalyst, for example $Bu_4NBr$.

NH-1,2,3-triazoles of formula (III) can be obtained by cycloaddition of tri-n-butyltin azide with mono- or disubstituted alkynes of formula (II):

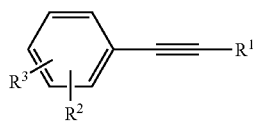

II wherein $R_1$, $R_2$ and $R_3$ are as defined above.

This cycloaddition reaction takes place under pressure and heating conditions according to known methods (S. Kozima, T. Itano, N. Mihara, K. Sisido, T. Isida, *J. Organomet. Chem.* 1972, 44, 117-126; T. Hitomi, S. Kozima, *J. Organomet. Chem.* 1977, 127, 273-280). Then, the tributylstannyl group is subsequently replaced by a proton under mild conditions.

The mono- or di-substituted alkynes (II) used in this synthesis may be obtained from commercial sources or may be prepared from the corresponding iodobenzene and monosubstituted alkyne (J. F. Nguefack, V. Bolitt, D. Sinou, *Tetrahedron Lett.* 1996, 37, 5527-5530) according to the reaction as shown below:

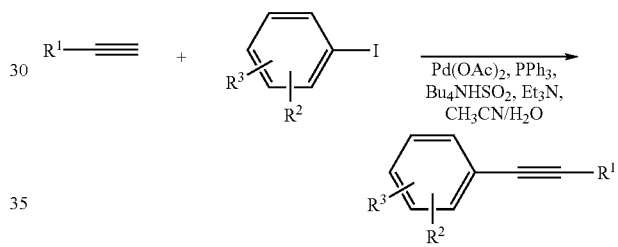

The obtained reaction products may, if desired, be purified by conventional methods, such as crystallisation, chromatography and trituration. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing a sigma-1 receptor mediated disease which method comprises administering to a patient in need of such a treatment a therapeutically effective amount of a compound of formula I or a pharmaceutical composition thereof.

Among the sigma-1 mediated diseases that can be treated or prevented are diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation, autoimmune diseases, especially neuropathic pain, inflammatory pain or other pain conditions involving allodynia and/or hyperalgesia. The compounds of the invention can also be employed as pharmacological tool or as anxiolytic or immunosuppressant.

The present invention further provides pharmaceutical compositions comprising a compound of this invention, or a pharmaceutically acceptable salt, isomer, prodrug or solvate thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

Example 1

Synthesis of 1-[3-[4-(p-chlorophenyl)-5-phenyl-([1,2,3]triazol-2-yl)propyl]-piperidine (compound 1)

Step A: A mixture of tri-n-butyltin azide (0.86 mL, 3.15 mmol) with the 4-chlorophenylethynylbenzene (3 mmol) was heated at 150° C. for 70 h in a sealed glass bottle. The resulting solution was purified by column chromatography (cyclohexane/AcOEt, 5:1) and recrystallized from (cyclohexane/AcOEt) to give 4-(p-chlorophenyl)-5-phenyl-1H(2H)-[1,2,3]triazole as a white solid (413 mg, 54% yield); m.p. 124-126° C. $^1$H NMR (200 MHz, CDCl$_3$, 25° C.) δ=7.51-7.46 (m, 4H), 7.38-7.35 (m, 3H), 7.31 (dt, $^3$J=8.6 Hz, $^4$J=$^5$J=2.2 Hz, 2H) ppm. ES-MS: m/z=278 [M$^+$+Na], 256 [M$^+$]. C$_{14}$H$_{10}$ClN$_3$ (255.70): caldc. C, 65.76; H, 3.94; N, 16.43. found C, 65.93; H, 3.84; N, 16.37.

Step B: To a solution of 4-(p-chlorophenyl)-5-phenyl-1H(2H)-[1,2,3]triazole (0.16 mmol) in acetonitrile (3 mL) was added K$_2$CO$_3$ (26 mg, 0.19 mmol) and Bu$_4$NBr (5 mg, 0.02 mmol). The mixture was stirred for 1 h at reflux temperature. Then 1,3-dibromopropane (38 mg, 0.19 mmol) was added and the mixture was stirred at reflux for 10 min. The resulting solution was filtered and the remaining solid material was washed with Et$_2$O (20 mL). Evaporation of the combined solutions afforded an oil residue. Column chromatography on silica gel of the oily crude eluting with cyclohexane/AcOEt (10:1) gave 1-[3-[4-(p-chlorophenyl)-5-phenyl-(-[1,2,3]triazol-2-yl)]-3-bromopropane (35 mg, 60% yield); $^1$H NMR (200 MHz, CDCl$_3$, 25° C.) δ=7.51-7.49 (2H, m), 7.47 (2H, dt, $^3$J=8.6 Hz, $^4$J=$^5$J=2.4 Hz), 7.38-7.34 (3H, m), 7.32 (2H, dt, $^3$J=8.6 Hz, $^4$J=$^5$J=2.4 Hz), 4.64 (2H, t, $^3$J=6.5 Hz), 3.49 (2H, t, $^3$J=6.5 Hz), 2.58 (2H, qt, $^3$J=6.5 Hz) ppm. ES-MS: m/z=379 (27), 377 (100), 375 (79) [M$^{+\bullet}$]; 296 (14) [M-79]; 268 (29) [M-109]; 212 (27) [M-165]; 165 (21) [M-212].

Step C: 41-[3-[4-(p-chlorophenyl)-5-phenyl-(-[1,2,3]triazol-2-yl)]-3-bromopropane (26 mg, 0.07 mmol) and piperidine (9 mg, 0.10 mmol) were refluxed in ethanol for 1 h in presence of dry sodium carbonate (11 mg, 0.10 mmol). The reaction mixture was then filtrated. The solid was washed with CH$_2$Cl$_2$. The combined filtrates was evaporated in vacuo. The resulting oil was then purified by chromatography on silica gel eluting with EtOAc to afford 1-[3-[4-(p-chlorophenyl)-5-phenyl-(-[1,2,3]triazol-2-yl)propyl]-piperidine (35 mg, 75% yield); $^1$H NMR (200 MHz, CDCl$_3$, 25° C.) δ=7.53-7.46 (4H, m), 7.39-7.31 (5H, m), 4.52 (2H, t, $^3$J=7.1 Hz), 2.46-2.39 (6H, m), 2.23 (2H, qt, $^3$J=7.2 Hz), 1.58 (4H, qt, $^3$J=5.5 Hz), 1.42 (2H, qt, $^3$J=5.5 Hz) ppm. ES-MS: m/z=382 (5), 381 (4), 380 (14) [M$^{+\bullet}$]; 98 (100) [M-283]; 84 (30) [M-297].

The compounds of examples 2-21 have been prepared as described for the example 1 using the appropriate mono- or disubstituted alkyne in Step A, the appropriate dibromoalkane in Step B and the appropriate NH-heterocycle or amine in Step C.

Example 2

1-[3-[4-(p-chlorophenyl)-5-phenyl-([1,2,3]triazol-2-yl)propyl]-imidazole (compound 2)

m.p. 122-124° C. $^1$H NMR (500 MHz, CDCl$_3$, 25° C.) δ=7.60 (1H, s), 7.54-7.52 (2H, m), 7.49 (2H, d, $^3$J=8.5 Hz), 7.40-7.38 (3H, m), 7.34 (2H, d, $^3$J=8.5 Hz), 7.10 (1H, s), 7.02

(1H, s), 4.48 (2H, t, $^3J$=6.5 Hz), 4.09 (2H, t, $^3J$=6.5 Hz), 2.49 (2H, qt, $^3J$=6.5 Hz) ppm. ES-MS: m/z=365 (13), 364 (8), 363 (36) [M$^{+\bullet}$]; 364 (12), 362 (38) [M-1]; 95 (82) [M-269]; 82 (100) [M-282]; 212 (27) [M-165]; 165 (21) [M-212].

Example 3

1-[3-[4-(3,4-dichlorophenyl)-5-phenyl-([1,2,3]triazol-2-yl)propyl]-pyrrolidine (compound 3)

$^1$H NMR (500 MHz, CDCl$_3$, 25° C.) δ=7.70 (1H, d, $^4J$=2.0 Hz), 7.51-7.49 (2H, m), 7.42-7.38 (4H, m), 7.33 (1H, dd, $^3J$=8.3 Hz, 4J=2.0 Hz), 4.56 (2H, t, $^3J$=7.0 Hz), 2.75-2.72 (6H, m), 2.37 (2H, qt, $^3J$=7.0 Hz), 1.87 (4H, qt, $^3J$=3.4 Hz) ppm. ES-MS: m/z=402 (1), 400 (1) [M$^{+\bullet}$]; 111 (20) [M-290]; 84 (100) [M-317]; 70 (19) [M-331].

Example 4

1-[3-[4-(2,4-dichlorophenyl)-5-p-tolyl-([1,2,3]triazol-2-yl)propyl]-piperidine (compound 4)

$^1$H NMR (500 MHz, CDCl$_3$, 25° C.) 6=): 7.44 (1H, d, 4J=2.2 Hz), 7.40 (1H, d, $^3J$=8.5 Hz), 7.36-7.33 (3H, m), 7.12 (2H, d, $^3J$=8.1 Hz), 4.54 (2H, t, $^3J$=7.1 Hz), 2.44-2.39 (6H, m), 2.34 (3H, s), 2.23 (2H, qt, $^3J$=7.1 Hz), 1.61-1.54 (4H, m), 1.46-1.42 (2H, m) ppm. ES-MS: m/z=98 (100) [M-331]; 84 (25) [M-345].

Example 5

4-[3-[4-(2,4-dichlorophenyl)-5-p-tolyl-([1,2,3]triazol-2-yl)propyl]-morpholine (compound 5)

$^1$H NMR (200 MHz, CDCl$_3$, 25° C.) δ=7.41 (1H, dd, 4J=2.4 Hz, $^5J$=0.4 Hz), 7.38 (1H, d, $^3J$=8.6 Hz, $^5J$=0.4 Hz), 7.33 (1H, dd, $^3J$=8.6 Hz, 4J=2.4 Hz), 7.32 (2H, dd, $^3J$=8.1 Hz, 4J=1.8 Hz), 7.10 (2H, ddd, $^3J$=8.1 Hz, 4J=1.8 Hz, $^5J$=0.5 Hz), 4.55 (2H, t, $^3J$=7.0 Hz), 3.69 (4H, t, 3J=4.7 Hz), 2.42-2.45 (2H, m), 2.32 (3H, s), 2.21 (2H, qt, $^3J$=7.0 Hz) ppm. ES-MS: m/z=431 [M$^{+\bullet}$].

Example 6

1-[3-[4-(p-chlorophenyl)-5-phenyl-([1,2,3]triazol-2-yl)propyl]-homopiperidine (compound 6)

$^1$H NMR (200 MHz, CDCl$_3$, 25° C.) δ=7.51-7.44 (4H, m), 7.37-7.33 (3H, m), 7.30 (2H, dt, $^3J$=8.8 Hz, $^4J$=$^5J$=2.3 Hz), 4.51 (2H, t, $^3J$=7.1 Hz), 2.67 (4H, t, $^3J$=5.5 Hz), 2.62 (2H, t, $^3J$=7.1 Hz), 2.20 (2H, qt, $^3J$=7.1 Hz), 1.68-1.55 (8H, m) ppm. ES-MS: m/z=395.1 [M$^{+\bullet}$].

Example 7

1-[3-[4-(3,4-dichlorophenyl)-5-phenyl-([1,2,3]triazol-2-yl)propyl]-imidazole (compound 7)

$^1$H NMR (200 MHz, CDCl$_3$, 25° C.) δ=7.73 (1H, d, $^4J$=1.8 Hz) 7.62 (1H, brs), 7.57-7.53 (2H, m), 7.47-7.41 (4H, m), 7.37 (2H, dd, $^3J$=8.4 Hz, $^4J$=2.0 Hz), 7.13 (1H, brs), 7.05 (1H, brs), 4.50 (2H, t, $^3J$=6.4 Hz), 4.12 (2H, t, $^3J$=6.4 Hz), 2.52 (2H, qt. $^3J$=6.4 Hz)ppm. ES-MS: m/z=398.1 [M$^{+\bullet}$].

Example 8

1-[3-[4-(3,4-dichlorophenyl)-5-phenyl-([1,2,3]triazol-2-yl)propyl]-homopiperidine (compound 8)

$^1$H NMR (200 MHz, CDCl$_3$, 25° C.) δ=7.64 (1H, d, $^4J$=1.8 Hz), 7.46-7.42 (2H, m), 7.36-7.31 (4H, m), 7.28 (2H, dd, $^3J$=8.8 Hz, $^4J$=1.8 Hz), 4.47 (2H, t, $^3J$=7.0 Hz), 2.65 (4H, t, $^3J$=4.5 Hz), 2.60 (2H, t, $^3J$=7.0 Hz), 2.19 (2H, qt, $^3J$=7.0 Hz), 1.55 (8H, brs)ppm. ES-MS: m/z=429.2 [M$^{+\bullet}$].

Example 9

1-[3-[4-(3,4-dichlorophenyl)-5-phenyl-([1,2,3]triazol-2-yl)propyl]-cyclohexylamine (compound 9)

$^1$H NMR (300 MHz, CDCl$_3$, 25° C.) δ=77.66 (1H, d, $^4J$=1.9 Hz), 7.49-7.44 (2H, m), 7.38-7.34 (4H, m), 7.30 (1H, dd, $^3J$=8.5 Hz, $^4J$=1.9 Hz), 4.59 (2H, t, $^3J$=7.0 Hz), 3.11 (2H, t, $^3J$=7.0 Hz), 2.96 (1H, tt, $^3J_{ax-ax}$=11.5 Hz, $^3J_{ax-eq}$=3.8 Hz), 2.65 (2H, qt. $^3J$=7.0 Hz), 2.19-2.15 (2H, m), 1.80-1.77 (2H, m), 1.61-1.49 (3H, m), 1.27-1.12 (4H, m) ppm. ES-MS: m/z=429.2 [M$^{+\bullet}$].

Example 10

1-[4-[4-(p-chlorophenyl)-5-phenyl-([1,2,3]triazol-2-yl)butyl]-piperidine (compound 10)

$^1$H NMR (300 MHz, CDCl$_3$, 25° C.) δ=7.51-7.44 (4H, m), 7.36-7.32 (3H, m), 7.30 (2H, dt, $^3J$=8.5 Hz, $^4J$=$^5J$=2.2 Hz), 4.46 (2H, t, $^3J$=7.2 Hz), 2.35-2.29 (6H, m), 2.03 (2H, qt, $^3J$=7.5 Hz), 1.60-1.51 (6H, m), 1.43-1.39 (2H, m) ppm. ES-MS: m/z=395.1 [M$^{+\bullet}$]. C$_{23}$H$_{27}$ClN$_4$×⅓ H$_2$O (419.6): caldc. C, 68.90; H, 6.96; N, 13.97. found C, 68.92; H, 7.09; N, 13.70.

Example 11

1-[2-[4-(p-chlorophenyl)-5-phenyl-([1,2,3]triazol-2-yl)ethyl]-piperidine (compound 11)

$^1$H NMR (300 MHz, CDCl$_3$, 25° C.) δ=7.51-7.44 (4H, m), 7.37-7.28 (5H, m), 4.59 (2H, t, $^3J$=7.5 Hz), 2.99 (2H, t, $^3J$=7.5 Hz), 2.49 (4H, t, $^3J$=5.4 Hz), 1.57 (4H, qt, $^3J$=5.4 Hz), 1.41 (2H, qt, $^3J$=4.5 Hz) ppm. ES-MS: m/z=367 [M$^{+\bullet}$]. C$_{21}$H$_{23}$ClN$_4$×⅓ Et$_2$O (391.6): caldc. C, 68.50; H, 6.78; N, 14.31. found C, 68.80; H, 6.63; N, 14.25.

Example 12

4-[2-[4-(p-chlorophenyl)-5-phenyl-([1,2,3]triazol-2-yl)ethyl]-morpholine (compound 12)

$^1$H NMR (300 MHz, CDCl$_3$, 25° C.) δ=7.54-7.47 (4H, m), 7.39-7.32 (5H, m), 4.62 (2H, t, 3J=7.0 Hz), 3.72 (4H, t, $^3J$=4.5 Hz), 3.04 (2H, t, $^3J$=7.0 Hz), 2.57 (4H, t, $^3J$=4.5 Hz) ppm. ES-MS: m/z=369.1 [M$^{+\bullet}$]. C$_{20}$H$_{21}$ClN$_4$O×⅓ Et$_2$O (393.6): caldc. C, 65.10; H 6.23; N, 14.24. found C, 64.80; H, 6.00; N, 14.36.

Example 13

1-[2-[4-(p-chlorophenyl)-5-phenyl-([1,2,3]triazol-2-yl)ethyl]-pyrrolidine (compound 13)

$^1$H NMR (400 MHz, CDCl$_3$, 25° C.) δ=7.51-7.49 (2H, m), 7.47 (2H, dt, $^3J$=8.4 Hz, $^4J$=$^5J$=2.1 Hz), 7.37-7.33 (3H, m), 7.30 (2H, dt, $^3J$=8.4 Hz, $^4J$=$^5J$=2.1 Hz), 4.60 (2H, t, 3J=7.2 Hz), 3.14 (2H, m, $^3J$=7.2 Hz), 2.59 (4H, m), 1.78 (4H, m) ppm. ES-MS: m/z=353.1 [M$^{+\bullet}$].

Example 14

1-[5-[4-(p-chlorophenyl)-5-phenyl-([1,2,3]triazol-2-yl)pentyl]-piperidine (compound 14)

$^1$H NMR (300 MHz, CDCl$_3$, 25° C.) δ=7.52-7.49 (2H, m), 7.47 (2H, dt, $^3J$=8.6 Hz, $^4J$=$^5J$=2.2 Hz), 7.38-7.34 (3H, m), 7.31 (2H, dt, $^3J$=8.6 Hz, 4J=$^5J$=2.2 Hz), 4.46 (2H, t, $^3J$=7.3 Hz), 2.39-2.23 (H, m), 2.05 (2H, t, $^3J$=7.3 Hz), 1.60-1.58 (6H, m), 1.43-1.38 (4H, m) ppm. ES-MS: m/z=409.2 [M$^{+\bullet}$].

Example 15

1-[3-[4-[(p-chlorophenyl)-5-phenyl-([1,2,3]triazol-2-yl)propyl]-pyrrolidine (compound 15)

$^1$H NMR (200 MHz, CDCl$_3$, 25° C.) δ=7.56-7.49 (4H, m), 7.39-7.30 (5H, m), 4.55 (2H, t, 3J=7.0 Hz), 3.42 (2H, t, $^3J$=6.7 Hz), 2.62-2.50 (6H, m), 2.26 (2H, qt, 3J=7.0 Hz), 1.82-1.76 (2H, m) ppm. ES-MS: m/z=367.1 [M$^{+\bullet}$].

Example 16

1-[3-[4-(p-chlorophenyl)-5-phenyl-([1,2,3]triazol-2-yl)propyl]-(4-phenyl)piperidine (compound 16)

$^1$H NMR (200 MHz, CDCl$_3$, 25° C.) δ=7.53-7.50 (2H, m), 7.48 (2H, dt, $^3J$=8.6 Hz, $^4J$=$^5J$=2.0 Hz), 7.38-7.34 (3H, m), 7.32 (2H, dt, $^3J$=8.6 Hz, $^4J$=$^5J$=2.0 Hz), 7.28-7.26 (2H, m), 7.22-7.18 (3H, m), 4.54 (2H, t, 3J=7.2 Hz), 3.04 (2H, dt, 2J=11.5 Hz, 3J=3.2 Hz), 2.50 (2H, t, $^3J$=7.2 Hz), 2.49-2.45 (1H, m), 2.26 (2H, qt, $^3J$=7.2 Hz), 2.05 (2H, td, $^2J$=$^3J$=11.5 Hz, $^3J$=3.2 Hz), 1.84-1.75 (4H, m) ppm. ES-MS: m/z=457.2 [M$^{+\bullet}$]. C$_{28}$H$_{29}$ClN$_4$ (457.0): caldc. C, 73.59; H, 6.40; N, 12.26. found C, 73.37; H, 6.21; N, 12.44.

Example 17

4-[3-[4-[(β-chlorophenyl)-5-phenyl-([1,2,3]triazol-2-yl)propyl]-morpholine (compound 17)

$^1$H NMR (200 MHz, CDCl$_3$, 25° C.) δ=7.47-7.39 (4H, m), 7.31-7.23 (5H, m), 4.47 (2H, t, $^3J$=7.0 Hz), 3.63 (4H, t, $^3J$=7.0 Hz), 2.43-2.36 (6H, m), 2.15 (2H, qt, $^3J$=7.0 Hz) ppm. C$_{21}$H$_{23}$ClN$_4$O (382.7): caldc. C, 65.87; H, 6.05; N, 14.63. found C, 65.45; H, 5.77; N, 14.28.

Example 18

1-[3-[4-(p-chlorophenyl)-5-phenyl-([1,2,3]triazol-2-yl)propyl]-(4-phenyl)piperazine (compound 18)

$^1$H NMR (400 MHz, CDCl$_3$, 25° C.) δ=7.54-7.51 (2H, m), 7.49 (2H, d, $^3J$=8.4 Hz), 7.39-7.37 (3H, m), 7.33 (2H, d, $^3J$=8.4 Hz), 7.27 (2H, t, $^3J$=8.8 Hz), 6.93 (2H, dd, $^3J$=8.8 Hz, $^3J$=7.1 Hz), 6.86 (1H, t, $^3J$=7.3 Hz), 4.57 (2H, t, $^3J$=7.0 Hz), 3.29 (4H, t, $^3J$=4.8 Hz), 2.63 (4H, t, $^3J$=4.8 Hz), 2.55 (2H, t, $^3J$=7.0 Hz), 2.28 (2H, qt, $^3J$=7.0 Hz) ppm. ES-MS: m/z=458.3 [M$^{+\bullet}$]. C$_{27}$H$_{28}$ClN$_5$ (458.0): caldc. C, 70.81; H, 6.16; N, 15.29. found C, 70.54; H, 5.96; N, 15.30

Example 19

1-[3-[4-methyl-5-phenyl-([1,2,3]triazol-2-yl)propyl]-piperidine (compound 19)

$^1$H NMR (200 MHz, CDCl$_3$, 25° C.) δ=7.65 (2H, dt, $^3J$=6.5 Hz, $^4J$=1.8 Hz), 7.45-7.31 (3H, m), 4.40 (2H, t, $^3J$=7.0 Hz), 2.45 (3H, s), 2.43-2.32 (6H, m), 2.12 (2H, qt, $^3J$=7.0 Hz), 1.55 (4H, qt, $^3J$=5.2 Hz), 1.44-1.39 (2H, m) ppm. ES-MS: m/z=285.2 [M$^{+\bullet}$+1]. C$_{17}$H$_{24}$N$_4$ (284.40): caldc. C, 71.29; H, 8.51; N, 19.70. found C, 71.58; H, 8.31; N, 19.60.

Example 20

1-[3-[4-phenyl-([1,2,3]triazol-2-yl)propyl]-piperidine (compound 20)

$^1$H NMR (200 MHz, CDCl$_3$, 25° C.) δ=7.74 (1H, S, H$_5$), 7.70 (2H, d, $^3J$=7.8 Hz), 7.38-7.29 (3H, m), 4.43 (2H, t, $^3J$=7.0 Hz), 2.29-2.26 (6H, m), 2.14 (2H, qt, $^3J$=7.0 Hz), 1.55-1.47 (4H, m), 1.36-1.33 (2H, m) ppm. ES-MS: m/z=271.3 [M$^{+\bullet}$+1]. C$_{16}$H$_{22}$N$_4$ (270.37): caldc. C, 71.08; H, 8.20; N, 20.72. found C, 70.84; H, 8.17; N, 20.89.

Example 21

1-[3-[4-(4-bromo-2-fluoro-phenyl-([1,2,3]triazol-2-yl)propyl]-piperidine (compound 21)

$^1$H NMR (300 MHz, CDCl$_3$, 25° C.) δ=7.92 (1H, d, $^5J_{H-F}$=4.2 Hz), 7.87 (1H, dd, $^3J$=8.8 Hz, $^4J_{H-F}$=7.6 Hz), 7.37-7.32 (2H, m), 4.51 (2H, t, $^3J$=7.1 Hz), 2.40-2.35 (6H, m), 1.57 (4H, qt, $^3J$=5.6 Hz), 1.53-1.40 (2H, m) ppm. ES-MS: m/z=367, 369 [M$^{+\bullet}$+1]. C$_{16}$H$_{20}$BrFN$_4$ (367.26): caldc. C, 52.33; H, 5.49; N, 15.26. found C, 51.94; H, 5.18; N, 15.44.

The examples 22-27 have been prepared as described for the example 1 starting from the corresponding alkynes and dibromoalkanes.

Example 22

1-[2-(4-phenyl-2H-[1,2,3]triazol-2-yl)-ethyl]-azepane (compound 22)

$^1$H NMR (300 MHz, CDCl$_3$, 25° C.) δ=7.75 (1H, s), 7.72-7.70 (2H, m), 7.37-7.32 (2H, m), 7.30-7.27 (1H, m), 4.47 (2H, t, $^3J$=6.7 Hz), 3.08 (2H, t, $^3J$=6.7 Hz), 2.65 (4H, t, $^3J$=5.2 Hz), 1.54-1.49 (8H, m) ppm. ES-MS: m/z=271.

Example 23 cyclohexyl-[3-(4-phenyl-2H-[1,2,3]triazol-2-yl)propyl]-amine (compound 23)

$^1$H NMR (400 MHz, CDCl$_3$, 25° C.) δ=7.80 (1H, s), 7.77-7.24 (2H, m), 7.41 (2H, tt, $^3J$=7.4 Hz, $^4J$=1.5 Hz), 7.32 (1H, tt, $^3J$=7.4 Hz, $^4J$=1.5 Hz), 4.53 (2H, t, $^3J$=6.8 Hz), 3.02-2.98 (1H, m), 2.64 (2H, t, $^3J$=6.8 Hz), 2.37 (1H, tt, $^3J$=10.4 Hz, $^3J$=3.7 Hz), 2.13 (2H, qt, $^3J$=6.8 Hz), 1.85-1.81 (2H, m), 1.69-1.67

(2H, m), 1.60-1.56 (1H, m), 1.20-1.00 (5H, m) ppm. EI-MS: m/z=284 (6); 241 (100); 186 (88); 98 (60).

Example 24

1-[4-(4-phenyl-2H-[1,2,3]triazol-2-yl)-butyl]-azepane (compound 24)

$^1$H NMR (300 MHz, CDCl$_3$, 25° C.) δ=7.82 (1H, s), 7.78 (2H, d, $^3$J=7.2 Hz), 7.42 (2H, t, $^3$J=7.2 Hz), 7.36-7.34 (1H, m), 4.47 (2H, t, $^3$J=7.3 Hz), 2.61-2.57 (4H, m), 2.50 (2H, t, $^3$J=7.3 Hz), 2.02 (2H, qt, $^3$J=7.3 Hz), 1.58-1.46 (10H, m) ppm. ES-MS: m/z=299.

Example 25

1-[3-(4-phenyl-2H-[1,2,3]triazol-2-yl)-propyl]-azepane (compound 25)

$^1$H NMR (300 MHz, CDCl$_3$, 25° C.) δ=7.79 (1H, s), 7.75 (2H, dt, $^3$J=7.2 Hz, $^4$J=1.5 Hz), 7.42 (2H, tt, $^3$J=7.2 Hz, $^4$J=1.5 Hz), 7.31 (1H, tt, $^3$J=7.2 Hz, $^4$J=1.5 Hz), 4.49 (2H, t, $^3$J=7.0 Hz), 2.62 (4H, t, $^3$J=5.5 Hz), 2.54 (2H, t, $^3$J=7.0 Hz), 2.14 (2H, qt, $^3$J=7.0 Hz), 1.61-1.54 (8H, m) ppm. ES-MS: m/z=285.

Example 26

4-[3-(4-phenyl-2H-1,2,3-triazol-2-yl)-propyl]-morpholine (compound 26)

$^1$H NMR (300 MHz, CDCl$_3$, 25° C.) δ=7.79 (1H, s), 7.74 (2H, d, $^3$J=6.9 Hz), 7.42-7.37 (2H, m), 7.34-7.28 (1H, m), 4.50 (2H, t, $^3$J=7.0 Hz), 2.67 (4H, t, $^3$J=4.7 Hz), 2.42-2.35 (6H, m), 2.14 (2H, qt, $^3$J=7.0 Hz) ppm. ES-MS: m/z=273.

Example 27

1-[2-(4-phenyl-2H-[1,2,3]triazol-2-yl)-ethyl]-piperidine (compound 27)

$^1$H NMR (300 MHz, CDCl$_3$, 25° C.) δ=7.82 (1H, s), 7.80-7.77 (2H, m), 7.45-7.40 (2H, m), 7.37-7.32 (1H, m), 4.59 (2H, t, $^3$J=7.2 Hz), 2.97 (2H, t, $^3$J=7.2 Hz), 2.48 (4H, t, $^3$J=5.2 Hz), 1.58 (4H, qt, $^3$J=5.2 Hz), 1.47-1.41 (2H, m) ppm. EI-MS: m/z=98 (100).

Example 28

1-[2-(4-phenyl-2H-[1,2,3]triazol-2-yl)-ethyl]-azepanium oxalate (compound 28)

1-[2-(4-Phenyl-[1,2,3]triazol-2-yl)-ethyl]azepane (compound 22) (0.25 mmol) was dissolved in ether (0.5 mL) and mixed with a solution of oxalic acid (0.25 mmol) in AcOEt (0.1 mL) to give 1-[2-(4-Phenyl-[1,2,3]triazol-2-yl)-ethyl] azepanium oxalate as a white precipitate which was filtered off and dried in vacuum. $^1$H NMR (500 MHz, DMSO$_{d6}$, 25° C.) δ=8.32 (1H, s), 7.85 (2H, d, $^3$J=7.4 Hz), 7.47 (2H, t, $^3$J=7.4 Hz), 7.38 (1H, t, $^3$J=7.4 Hz), 4.78 (2H, t, $^3$J=6.2 Hz), 3.52 (2H, sw), 3.09 (4H, sw), 1.70 (4H, sw), 1.55 (4H, sw) ppm. ES-MS m/z=271.0; C$_{18}$H$_{24}$N$_4$O$_4$×½ H$_2$O (369.4): caldc. C, 58.52; H, 6.82; N, 15.17. found C, 58.08; H, 6.61; N, 14.71.

The examples 29-33 have been prepared as described for the example 28 starting from the corresponding amine derivatives.

Example 29 cyclohexyl-[3-(4-phenyl-2H-1,2,3]triazol-2-yl)propyl]-ammonium oxalate (compound 29)

$^1$H NMR (300 MHz, DMSO$_{d6}$, 25° C.) δ=8.25 (1H, s), 7.81 (2H, d, $^3$J=7.2 Hz), 7.45 (2H, t, $^3$J=7.2 Hz), 7.38-7.33 (1H, m), 4.54 (2H, t, $^3$J=7.1 Hz), 2.99-2.94 (3H, m), 2.21 (2H, t, $^3$J=7.1 Hz), 1.93 (2H, sw), 1.70 (2H, sw), 1.58-1.54 (1H, m), 1.23-1.12 (5H, m) ppm. ES-MS m/z=285.0; C$_{19}$H$_{26}$N$_4$O$_4$ (374.2): caldc. C, 60.95; H, 7.00; N, 14.96. found C, 60.60; H, 7.29; N, 14.77.

Example 30

1-[4-(4-phenyl-2H-[1,2,3]triazol-2-yl)-butyl]-azepanium oxalate (compound 30)

$^1$H NMR (400 MHz, DMSO$_{d6}$, 25° C.) δ=8.21 (1H, s), 7.79 (2H, dt, $^3$J=7.3 Hz, $^4$J=1.5 Hz), 7.42 (2H, td, $^3$J=7.3 Hz, $^4$J=1.5 Hz), 7.33 (1H, tt, $^3$J=7.3 Hz, $^4$J=1.5 Hz), 4.45 (2H, t, $^3$J=7.1 Hz), 3.12 (4H, sw), 3.06-3.02 (2H, m), 1.89 (2H, qt, $^3$J=7.1 Hz), 1.70 (4H, sw), 1.64-1.59 (2H, m), 1.53 (4H, sw) ppm. ES-MS m/z=299.0; C$_{20}$H$_{28}$N$_4$O$_4$×½ H$_2$O (497.46): caldc. C, 60.59; H, 7.12; N, 14.13. found C, 60.56; H, 7.29; N, 13.81.

Example 31

1-[3-(4-phenyl-2H-[1,2,3]triazol-2-yl)-propyl]-azepanium oxalate (compound 31)

$^1$H NMR (400 MHz, DMSO$_{d6}$, 25° C.) δ=8.25 (1H, s), 7.81 (2H, d, $^3$J=7.4 Hz), 7.43 (2H, t, $^3$J=7.4 Hz), 7.34 (1H, t, $^3$J=7.3 Hz), 4.51 (2H, t, $^3$J=6.7 Hz), 3.15 (4H, sw), 3.07 (2H, m), 2.27 (2H, m), 1.72 (4H, sw), 1.54 (4H, sw) ppm. ES-MS m/z=285.0; C$_{19}$H$_{26}$N$_4$O$_4$×2H$_2$O×½ C$_2$H$_2$O$_4$ (455.4): caldc. C, 54.91; H, 6.68; N, 12.81. found C, 54.97; H, 6.31; N, 13.25.

Example 32

4-[3-(4-phenyl-2H-[1,2,3]triazol-2-yl)-propyl]-morpholin-4-ium oxalate (compound 32)

$^1$H NMR (400 MHz, DMSO$_{d6}$, 25° C.) δ=8.26 (1H, s), 7.84 (2H, dt, $^3$J=7.2 Hz, $^4$J=1.4 Hz), 7.46 (2H, tt, $^3$J=7.2 Hz $^4$J=1.4 Hz), 7.37 (1H tt, $^3$J=7.2 Hz $^4$J=1.4 Hz), 4.52 (2H, t, $^3$J=7.3 Hz), 3.69 (4H, sw), 2.83 (4H, sw), 2.78 (2H, t, $^3$J=7.8 Hz), 2.20 (2H, qt. $^3$J=7.3 Hz) ppm. ES-MS m/z=273.0; C$_{17}$H$_{22}$N$_4$O$_5$×½ H$_2$O (462.4): caldc. C, 54.98; H, 6.24; N, 15.09. found C, 54.75; H, 5.90; N, 14.81.

Example 33

1-[2-(4-phenyl-2H-[1,2,3]triazol-2-yl)-ethyl]-piperidinium oxalate (compound 33)

$^1$H NMR (300 MHz, DMSO$_{d6}$, 25° C.) δ=8.31 (1H, s), 7.83 (2H, d, $^3$J=8.1 Hz), 7.46 (2H, t, $^3$J=8.1 Hz), 7.39-7.34 (1H, m), 4.77 (2H, t, $^3$J=6.0 Hz), 1.60 (4H, sw), 1.45 (2H, sw) ppm. ES-MS m/z=257.3; C$_{17}$H$_{22}$N$_4$O$_5$×½C$_2$H$_2$O$_4$ (391.4): caldc. C, 55.24; H, 5.92; N, 14.31. found C, 55.59; H, 5.86; N, 14.64.

BIOLOGICAL ACTIVITY EXAMPLES

Some of the compounds synthesized according to the procedures described above were tested for their activity as sigma-1 inhibitors. The following protocol was followed:

Brain membrane preparation and binding assays for the 61-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 µL of [$^3$H](+)-pentazocine (final concentration of 0.5 nM), 900 µL of the tissue suspension to a final assay volume of 1 mL and a final tissue concentration of approximately 30 mg tissue net weight/mL. Non-specific binding was defined by addition of a final concentration of 1 µM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

DeHaven-Hudkins, D. L., L. C. Fleissner, and F. Y. Ford-Rice, 1992, Characterization of the binding of [$^3$H](+)pentazocine to 6 recognition sites in guinea pig brain, *Eur. J. Pharmacol.* 227, 371-378.

Lowry, O. H., N. J. Rosebrough, A. L. Farr, and R. J. Randall, 1951, Protein measurement with the Folin phenol reagent, *J. Biol. Chem.*, 193, 265.

The results are summarized in the following table I:

| compound no. | Sigma-1 Inhibition percent (0.1 µM) | Sigma-1 Inhibition percent (0.01 µM) |
|---|---|---|
| 6 | 52.5 | 36.5 |
| 10 | 59.1 | 26.1 |
| 19 | 78.5 | 31.2 |
| 20 | 82.2 | 43.6 |
| 21 | 83.4 | 25.8 |

The invention claimed is:
1. A compound of the formula I:

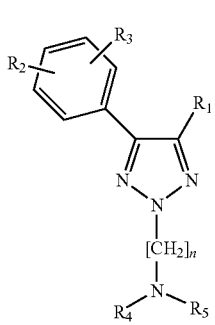

wherein
$R_1$ is selected from the group consisting of hydrogen, $C_1$-$C_6$ alkyl and substituted or unsubstituted aryl;
$R_2$ and $R_3$ are independently selected from the group consisting of hydrogen and halogen;
$R_4$ and $R_5$ are independently selected from the group consisting of hydrogen, $C_1$-$C_6$ alkyl and cycloalkyl, or form, together with the nitrogen to which they are attached, a substituted or unsubstituted heterocyclyl group; with the proviso that $R_4$ and $R_5$ are not both hydrogen,
n is an integer selected from 1, 2, 3, 4, 5, 6, 7 and 8,
or a pharmaceutically acceptable salt, or stereoisomer thereof.

2. The compound according to claim 1 wherein $R_1$ is hydrogen, $C_1$-$C_3$ alkyl, unsubstituted phenyl or a phenyl substituted by a $C_1$-$C_3$ alkyl.

3. The compound according to claim 2 wherein $R_2$ and $R_3$ are independently selected from the group consisting of hydrogen and halogen.

4. The compound according to claim 1 wherein one of $R_2$ and $R_3$ is in the para position of the phenyl group.

5. The compound according to claim 1 wherein $R_4$ and $R_5$ form, together with the nitrogen to which they are attached, a substituted or unsubstituted heterocyclyl group.

6. The compound according to claim 1 wherein n is an integer selected from 2, 3, 4, 5 and 6.

7. The compound according to claim 1 which is:
1-{3-[4-(4-chloro-phenyl)-5-phenyl-[1,2,3]triazol-2-yl]-propyl}-piperidine;
1-[3-[4-(p-chlorophenyl)-5-phenyl-([1,2,3]triazol-2-yl)propyl]-imidazole;
1-[3-[4-(3,4-dichlorophenyl)-5-phenyl-([1,2,3]triazol-2-yl)propyl]-pyrrolidine;
1-{3-[4-(2,4-dichloro-phenyl)-5-p-tolyl-[1,2,3]triazol-2-yl]-propyl}-piperidine;
4-{3-[4-(2,4-dichloro-phenyl)-5-p-tolyl-[1,2,3]triazol-2-yl]-propyl}-morpholine;
1-[3-[4-(p-chlorophenyl)-5-phenyl-([1,2,3]triazol-2-yl)propyl]-homopiperidine;
1-[3-[4-(3,4-dichlorophenyl)-5-phenyl-([1,2,3]triazol-2-yl)propyl]-imidazole;
1-[3-[4-(3,4-dichlorophenyl)-5-phenyl-([1,2,3]triazol-2-yl)propyl]-homopiperidine;
cyclohexyl-[3-[4-(3,4-dichlorophenyl)-5-phenyl-([1,2,3]triazol-2-yl)propyl]-amine
1-{4-[4-(4-chloro-phenyl)-5-phenyl-[1,2,3]triazol-2-yl]-butyl}-piperidine;
1-{2-[4-(4-chloro-phenyl)-5-phenyl-[1,2,3]triazol-2-yl]-ethyl}-piperidine;

4-{2-[4-(4-chloro-phenyl)-5-phenyl-[1,2,3]triazol-2-yl]-ethyl}-morpholine;
1-[2-[4-(p-chlorophenyl)-5-phenyl-([1,2,3]triazol-2-yl)ethyl]-pyrrolidine;
1-{5-[4-(4-chloro-phenyl)-5-phenyl-[1,2,3]triazol-2-yl]-pentyl}-piperidine;
4-(4-chloro-phenyl)-5-phenyl-2-(3-pyrrolidin-1-yl-propyl)-2H-[1,2,3]triazole;
1-{3-[4-(4-chloro-phenyl)-5-phenyl-[1,2,3]triazol-2-yl]-propyl}-4-phenyl-piperidine;
4-{3-[4-(4-chloro-phenyl)-5-phenyl-[1,2,3]triazol-2-yl]-propyl}-morpholine;
1-{3-[4-(4-chloro-phenyl)-5-phenyl-[1,2,3]triazol-2-yl]-propyl}-4-phenyl-piperazine;
1-[3-(4-methyl-5-phenyl-[1,2,3]triazol-2-yl)-propyl]-piperidine;
1-[3-(4-phenyl-[1,2,3]triazol-2-yl)-propyl]-piperidine;
1-{3-[4-(4-bromo-2-fluoro-phenyl)-[1,2,3]triazol-2-yl]-propyl}-piperidine;
1-[2-(4-phenyl-2H-[1,2,3]triazol-2-yl)-ethyl]-azepane;
cyclohexyl-[3-(4-phenyl-2H-[1,2,3]triazol-2-yl)propyl]-amine;
1-[4-(4-phenyl-2H-[1,2,3]triazol-2-yl)-buty]-azepane;
1-[3-(4-phenyl-2H-[1,2,3]triazol-2-yl)-propyl]-azepane;
4-[3-(4-phenyl-2H-[1,2,3]triazol-2-yl)-propyl]-morpholine;
1-[2-(4-phenyl-2H-[1,2,3]triazol-2-yl)-ethyl]-piperidine;
or a pharmaceutically acceptable salt, or isomer thereof.

8. The compound according to claim 1 which is an oxalic salt thereof.

9. The compound according to claim 8 which is:
1-[2-(4-phenyl-2H-[1,2,3]-triazol-2-yl)-ethyl]-azepanium oxalate;
cyclohexyl-[3-(4-phenyl-2H-[1,2,3]-triazol-2-yl)propyl]-ammonium oxalate;
1-[4-(4-phenyl-2H-[1,2,3]-triazol-2-yl)-butyl]-azepanium oxalate;
1-[3-(4-phenyl-2H-[1,2,3]-triazol-2-yl)-propyl]-azepanium oxalate;
4-[3-(4-phenyl-2H-[1,2,3]-triazol-2-yl)-propyl]-morpholin-4-ium oxalate;
1-[2-(4-phenyl-2H-[1,2,3]-triazol-2-yl)-ethyl]-piperidinium oxalate.

10. A process for the preparation of a compound of formula (I), as defined in claim 1 or a salt, or stereoisomer, thereof, which comprises the alkylation reaction of a compound NHR$_4$R$_5$ with a compound of formula (IV):

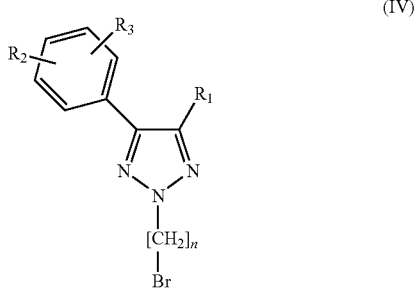

wherein:
R$_1$ is selected from the group consisting of hydrogen, C$_1$-C$_6$ alkyl and substituted or unsubstituted aryl;
R$_2$ and R$_3$ are independently selected from the group consisting of hydrogen and halogen;
R$_4$ and R$_5$ are independently selected from the group consisting of hydrogen, C$_1$-C$_6$ alkyl and cycloalkyl, or form, together with the nitrogen to which they are attached, a substituted or unsubstituted heterocyclyl group; and
n is an integer selected from 1, 2, 3, 4, 5, 6, 7 and 8,
with the proviso that R$_4$ and R$_5$ are not both hydrogen.

11. The process according to claim 10 wherein the compound of formula (IV) is prepared by alkylation of the compound of formula (III):

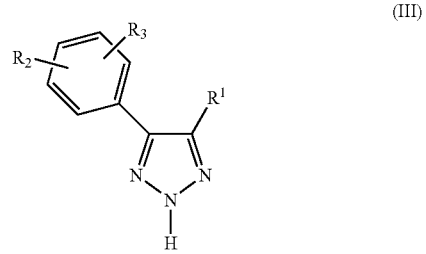

with an n-alkyl di-bromide of formula [Br—(—CH$_2$—)$_n$—Br];
wherein R$_1$, R$_2$, R$_3$ and n are as defined in claim 10.

12. The process according to claim 11 wherein the compound of formula (III) is prepared by cycloaddition of tri-n-butyltin azide with a compound of formula (II):

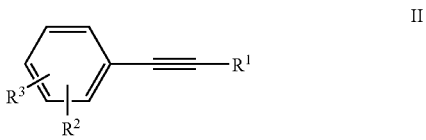

wherein R$_1$, R$_2$ and R$_3$ are as defined in claim 10.

13. A pharmaceutical composition which comprises a compound as defined in claim 1 or a pharmaceutically acceptable salt, or stereoisomer thereof, and a pharmaceutically acceptable carrier, adjuvant or vehicle.

14. A method of treating a disease selected from cocaine addiction, amphetamine addiction, depression and pain comprising administering to a patient in need of such a treatment a therapeutically effective amount of a compound of formula (I) as defined in claim 1 or a pharmaceutical composition thereof.

15. The compound according to claim 4 wherein R$_2$ and R$_3$ are independently selected from hydrogen and chloride.

16. The compound according to claim 5 wherein the heterocyclyl group is selected from the group consisting of piperidine, piperazine, imidazole, pyrrolidine, morpholine and azepane.

17. The method according to claim 14, wherein the pain is selected from neuropathic, inflammatory, allodynia and hyperalgesia.

* * * * *

UNITED STATES PATENT AND TRADEMARK OFFICE
CERTIFICATE OF CORRECTION

PATENT NO. : 8,193,223 B2
APPLICATION NO. : 12/514213
DATED : June 5, 2012
INVENTOR(S) : Nadine Jagerovic It is certified that error appears in the above-identified patent and that said Letters Patent is hereby corrected as shown below:

Column 3, Line 46 now reads "...treatment of diarrhoea,..."
Should read "...treatment of diarrhea,..."

Column 3, Line 52 now reads "...tardive diskinesia,..."
Should read "...tardive dyskinesia,..."

Column 8, Line 61 now reads "...prevented are diarrheoa,..."
Should read "...prevented are diarrhea,..."

Column 8, Line 67 to Column 9, Line 1 now reads "...tardive diskinesia,..."
Should read "...tardive dyskinesia,..."

Column 9, Line 20 now reads "...tablets, capsules, syrops..."
Should read "...tablets, capsules, syrups..."

Column 17, Line 8 now reads "...for the 61- Receptor..."
Should read "...for the σ1-Receptor..."

Signed and Sealed this
Eighteenth Day of December, 2012

David J. Kappos
*Director of the United States Patent and Trademark Office*